United States Patent [19]
Gopakumaran et al.

[11] Patent Number: 5,971,933
[45] Date of Patent: Oct. 26, 1999

[54] METHOD AND APPARATUS TO CORRECT FOR ELECTRIC FIELD NON-UNIFORMITY IN CONDUCTANCE CATHETER VOLUMETRY

[75] Inventors: Balakrishnan Gopakumaran, Shaker Heights; John H. Petre, Cleveland Heights, both of Ohio; Peter K. Osborn, West Allis; Paul Schluter, Whitefish Bay, both of Wis.

[73] Assignees: Cleveland Clinic Foundation, Cleveland, Ohio; Marquette Medical Systems, Milwaukee, Wis.

[21] Appl. No.: 08/920,345

[22] Filed: Aug. 27, 1997

Related U.S. Application Data

[60] Provisional application No. 60/026,222, Sep. 17, 1996.

[51] Int. Cl.$^6$ ........................................... A61B 5/029
[52] U.S. Cl. ................................................ 600/526
[58] Field of Search ...................... 607/29; 600/505–508, 600/547, 526

[56] References Cited

U.S. PATENT DOCUMENTS

| | | | |
|---|---|---|---|
| 4,674,518 | 6/1987 | Salo | 600/547 |
| 4,840,182 | 6/1989 | Carlson | 600/507 |
| 4,951,682 | 8/1990 | Petre . | |

Primary Examiner—William E. Kamm
Assistant Examiner—George R. Evanison
Attorney, Agent, or Firm—Michael Best & Friedrich LLP

[57] ABSTRACT

A method of determining cardiac volume including the steps of positioning a catheter in a blood-filled chamber of a patient's heart. The catheter comprises an elongated body having a distal end, a proximal end, a plurality of spaced electrodes arrayed on the outer surface of the catheter and spaced apart a predetermined distance from each other to define a distal electrode, a proximal electrode and a plurality of pairs of adjacent electrodes between the distal and proximal electrodes to define volume segments within the chamber. The method includes the steps of providing a constant alternating current to the distal and proximal electrodes, measuring the potential between pairs of electrodes located between a distal and proximal electrodes while the distal and proximal electrodes are energized with the constant amplitude alternating current; determining a set of correction factors from the measured raw segmental volumes and catheter curvature; and correcting for field non-uniformity by multiplying the raw volumes by the set of correction factors.

16 Claims, 8 Drawing Sheets

METHOD AND APPARATUS TO CORRECT FOR ELECTRIC FIELD NON-UNIFORMITY IN CONDUCTANCE CATHETER VOLUMETRY

This application is related to U.S. Provisional Application Ser. No. 60/026,222 filed Sep. 17, 1996.

BACKGROUND OF THE INVENTION

This invention relates to cardiac monitoring and more particularly to a method and apparatus for determining cardiac volume.

It is highly beneficial to monitor in real-time, the beat-to-beat stoke volume, ejection fraction and ventricular pressure-volume loops in patients undergoing cardiac surgery. Monitoring these parameters allows for better evaluation of the physiological status of these patients.

Figure 1:
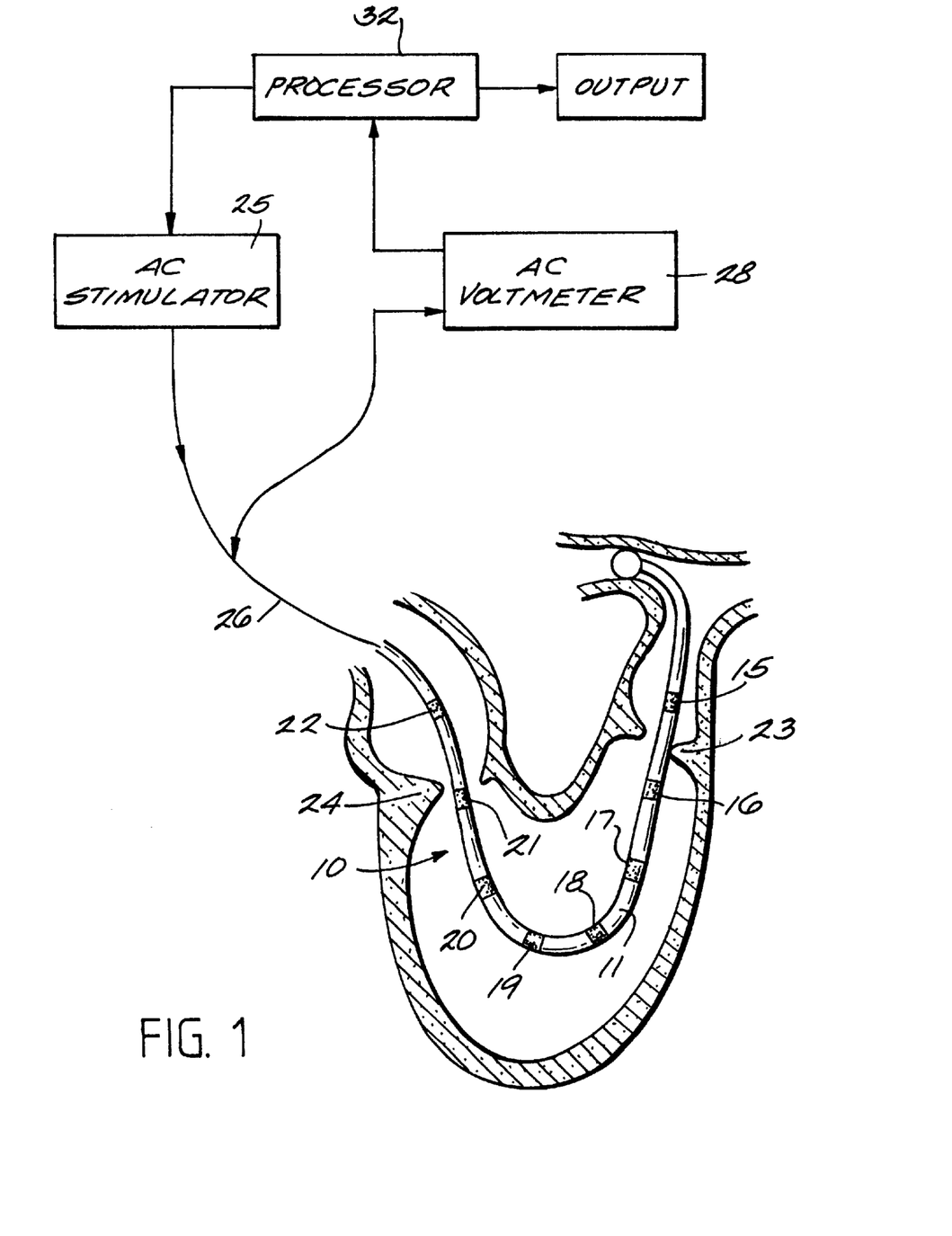
FIG. 1 schematically illustrates a conductance catheter in the right ventricle of a human heart.

There are several known methods of measuring cardiac output including echocardiography, contrast angiography and conductance catheter method. Of these, the conductance catheter method can potentially measure the absolute ventricular volume continuously in real time. Conductance catheters may comprise a modified Swan-Ganz catheter, for example, with a set of equidistant, metallic ring electrodes at the distal end. The Catheter is inserted into the patient's ventricle and a constant electrical current having a fixed frequency is applied to spaced apart exciting electrodes to establish a constant-current electric field within the blood volume of the ventricle. The spaced apart electrodes between the exciting electrodes (sensing electrodes) divide the ventricular volume into parallel segments as shown in FIG. 1. Voltage signals at pairs of spaced electrodes disposed between the exciting electrodes are sampled. This provides a potential drop ($V_i$) across these volume segments. Knowing $V_i$ and the constant current (I) injected by the exciting electrodes, the resistance across the volume segments ($R_i$) can be computed as follows:

$$R_i = V_i/I \quad (1)$$

The segmental resistances can be related to the volume of each segment by the expression:

$$\text{Vol}_i = \rho L^2/R_i \quad (2)$$

where $\text{Vol}_i$=Volume of the $i^{th}$ segment, $\rho$=blood resistivity,

L=spacing between the electrodes, and $R_i$=Resistance of the $i^{th}$ segment.

Conductive catheter methods of cardiac output measurements are disclosed in U.S. Pat. Nos. 4,674,518; 4,721,115; 4,898,176; 4,491,682, and 5,000,190. A method of determining blood resistivity is disclosed in co-pending application Ser. No. 08/701,177, filed Aug. 2, 1996, which is incorporated by reference herein.

From the segmental volumes, the total volume can be determined from the expression $$\text{Vol tot} = \sum_{i=1}^{n} \text{Vol}_i \quad (3)$$

where n=total number of volume segments.

Prior attempts to measure ventricular volume with the conductance catheter have mostly been confined to the left ventricle. Under clinical conditions, however, measurement of the right ventricle would be preferable, because the right side of the heart is more easily accessible than the left side. Also, the lower pressure in the right side of the heart and the greater clinical experience with right-side catheterization make it less dangerous to use the catheter on the right side compared to the left side. For these reasons, it is desirable to provide a conductance-catheter measuring method and apparatus for measuring right-ventricular volume.

Figure 2:
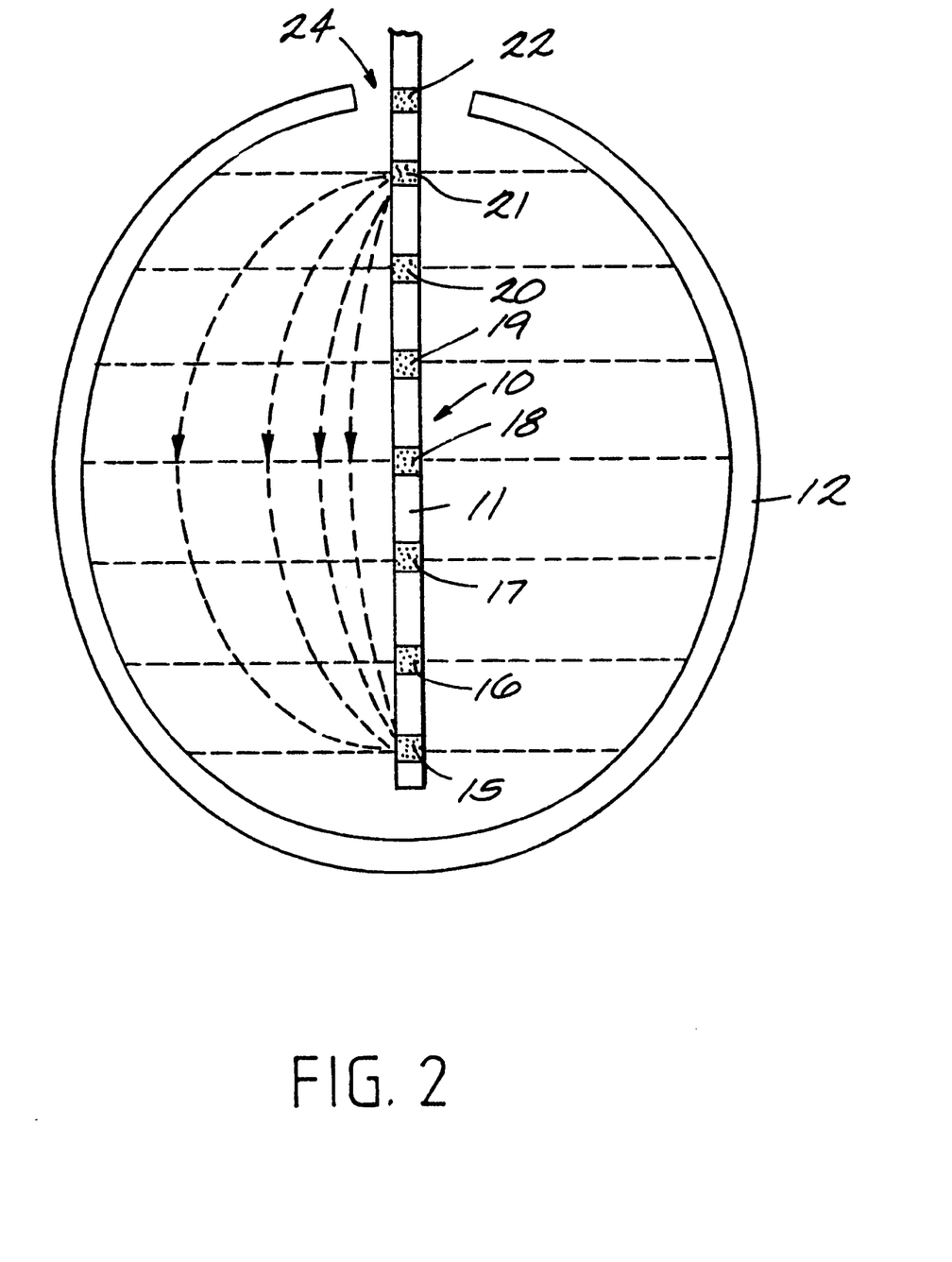
FIG. 2 shows the position of a conductance catheter in the left ventricle of a human heart.

Various studies have shown that there are four main sources of error in conductance-catheter measurements. These are:

1. Electric field non-uniformity. Equation (2) above is based on a uniform electric field. In actual practice, the electric field created by a conductance catheter is not uniform, and this causes the measurement of segmental volume to be inaccurate.
2. Leakage of current through surrounding tissues. Some of the injected conductance catheter current leaks out through the surrounding tissues, such as, cardiac and lung tissues, so that the electric field is no longer confined to the blood volume of the ventricle. This also introduces errors in the measurement of segmental resistances.
3. Catheter curvature. The catheter assumes a curved orientation in the right ventricle as shown in FIG. 2. The curved orientation of the catheter coupled with the non-uniformity of the electric field results in erroneous measurement of segmental volumes.
4. Blood resistivity changes. Blood resistivity changes primarily due to changes in hematocrit, temperature and blood velocity, which are not uncommon in cardiac patients undergoing surgery. Hence, measurement errors can result if blood conductivity changes are not monitored.

SUMMARY OF THE INVENTION

It is an object of the invention to provide a new and improved method and apparatus for measuring cardiac volume.

Another object of the invention is to provide a method and apparatus for determining cardiac volume by the conductance catheter method in which errors introduced by electric field non-uniformity are corrected.

These and other objects and advantages of the present invention will become more apparent from the detailed description thereof taken with the accompanying drawings.

In general terms, the invention comprises a method of determining cardiac volume including the steps of positioning a catheter in a blood-filled chamber of a patient's heart. The catheter comprises an elongated body having a distal end, a proximal end, a plurality of spaced electrodes arrayed on the outer surface of the catheter and spaced apart a predetermined distance from each other to define a distal electrode, a proximal electrode and a plurality of pairs of adjacent electrodes between the distal and proximal electrodes to define volume segments within the chamber. The method includes the steps of providing a constant alternating current to the distal and proximal electrodes, measuring the potential $V_1$ between pairs of electrodes located between the distal and proximal electrodes while the distal and proximal electrodes are energized with the constant alternating current; determining uncorrected segment volumes; and determining a set of correction factors from the measured uncorrected segmental volumes and catheter curvature; and correcting for field non-uniformity by multiplying the uncorrected volumes by the set of correction factors.

DETAILED DESCRIPTION OF THE PREFERRED EMBODIMENT

FIG. 1 schematically illustrates a conductance catheter 10 positioned in a blood filled space, such as a heart ventricle 12. The catheter 10 is of the type used in the conductance catheter method and apparatus for determining cardiac output. In particular, the catheter comprises an elongated body 11 having a plurality of axially extending lumens. The body 11 is formed of a flexible, plastic, electrically insulating material and may have a stiffening member extending through one of the lumens. A plurality of band electrodes 15–22 are mounted on the outer surface of the body 11, preferably in an equi-spaced fashion. The electrodes 15 and 22, which are positioned just outside the pulmonic or aortic valve 23 and the atrioventricular (AV) valve 24, are exciting electrodes and the intermediate electrodes 16–21 are sensing electrodes as shown in FIG. 1. Electrodes 15 and 22 are preferably chosen as the exciting electrodes to minimize leakage current and such that the volume of the entire ventricular chamber is measured.

The cardiac volume determining apparatus includes means for providing an alternating, electrical stimulation. In the preferred embodiment, the stimulator is a constant alternating current, stimulator 25. Separate conductors 26 connect stimulator 25 to each electrode 15–22 so that the alternating current can be applied to any selected pair of electrodes. Electrical parameter measuring means, which, in the preferred embodiment is an alternating current volt meter 28, is connected by separate conductors 30 across each pair of sensing electrodes 16–21 for measuring the voltage drop between each successive pair of electrodes. Means for determining the volume of ventricle 12 comprises a processor 32 coupled to the volt meter 28 for receiving the voltage signals between each pair of adjacent electrodes 16–21 within the ventricle 12.

While the preferred embodiment includes a constant current stimulator 25 and a voltmeter 28 connected respectively to the exciting electrodes and to the pairs of measuring electrodes, the invention also contemplates the appreciation of a constant voltage to the exciting electrodes and means for measuring current flow connected to the pairs of measuring electrodes for measuring the current flow therebetween.

The processor 32 is programmed to determine absolute ventricular volume from expression (2) above, using the leakage current, electric field non-uniformity and catheter curvature corrections discussed below, from the known constant current, I, applied by current source 25 to the exciting electrodes, the voltage signals, V, measured by the volt meter 28 across pairs of electrodes between the exciting electrodes, the known distance, L, between the sensing electrodes and the resistivity, $\rho$, of the blood and empirically derived correction factors.

Figure 3:
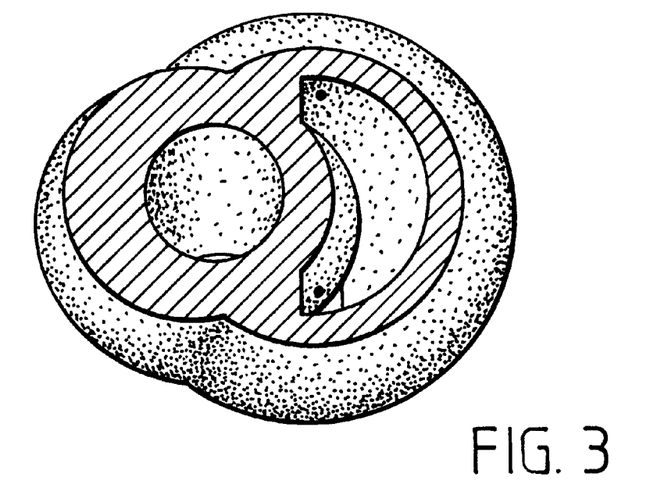
FIG. 3 shows a three dimensional model of a human heart.
Figure 4:
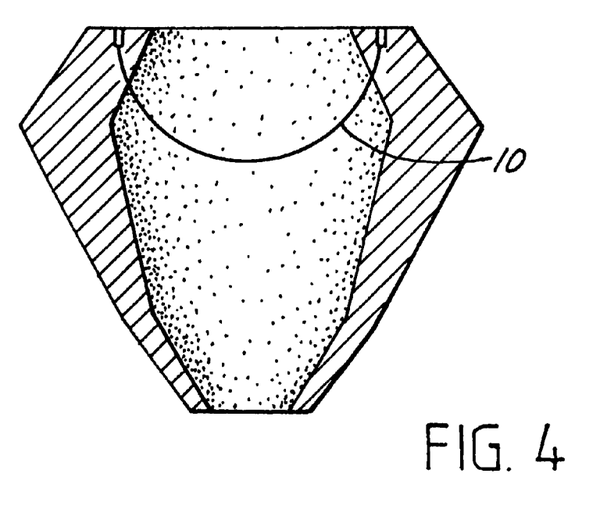
FIG. 4 shows the model of right ventricle with a curved conductance catheter.

In order to determine the quantitative and qualitative factors which introduce errors into the measurement of right ventricular volume, a three dimensional finite element model of the heart was developed along with a model of the curved catheter and the exciting electrodes as shown in FIGS. 3 and 4. Constant current loads of 20 $\mu$A at 2 KHz were applied through the exciting electrodes and the electric field distribution within the model was solved using finite element methods. Volume measurements were made with the simulated catheter. The electric potential distribution within any conductive medium due to a constant-current source is given by Poisson's equation:

$$\nabla(\overline{\sigma}\nabla V) = -I \qquad (4)$$

where $\nabla$=Laplacian operator,

V=potential,

I—current Injected, and $\overline{\sigma}$=the conductivity of the medium

An analytical solution for equation (4) can be found only for simple geometries. Finite element methods must be used to solve for Poisson's equation in complex geometries such as that of the heart. This can be accomplished using any suitable commercially available software such as, for example, ANSYS (Version: IRIS4D, 5.1, Swanson Analysis Systems, Inc., Houston, Pa.) for finite element analysis. Although various methods for finite element analysis may be used, in the instant case, the general steps adopted are:

1. Create the geometry of the model using preprocessing tools.
2. Assign material properties (resistivity) to different regional of the model.
3. Divide the model into a finite number of elements by a process called "meshing".
4. Apply current sources at the appropriate points (exciting electrodes) in the model.
5. Solve for the potential distribution within the model.
6. Obtain results and do post processing.

The heart model shown in FIGS. 3 and 4 includes the right and left ventricular chambers, the left and right ventricular walls, and the septum. In order to develop correction methods for the main sources of error such that they would apply to hearts of any general shape, no attempt was made to model an exact geometry of the heart. Instead, a heart model with shapes of the ventricular chambers typical of a normal heart as built. The model was built from conical primitives with linear and angular dimensions chosen from the literature. The thickness of the chamber walls, the volumes of the ventricular chambers, and the curvature of the chambers correspond to those of a normal heart. The exciting electrodes were modeled so that they were positioned approximately at the center of the atrioventricular valve 24 and the pulmonic valve 23. The conductance catheter establishes an alternating constant-current electric field as shown in FIG. 2. A direct current source cannot be used because blood is highly resistive at very low frequencies of excitation. At low frequencies, the interference from electrocardiograph signals is also high. In addition the lower the frequency the lower the amplitude of current that can be injected into the body safety, which increases the demand from the electronic device that measures the segmental voltage. At high frequencies, however, the tissues resistivity decreases and more of the injected current leaks out of the blood region. Thus, the frequency of stimulation of the catheter's electric field is chosen taking into consideration all of the above factors. The electric excitation employed was 20 $\mu$A at 2 KHz which is the signal specification of the Marquette Medical Systems conductance catheter measuring module which was used for the experimental verification of computer-simulation results. For this excitation frequency, cardiac tissues and blood are predominately resistive. Though cardiac tissue has been shown to be anisotropic, isotropic properties were assumed for the cardiac tissue for simplicity and an average value of tissue resistivity was used in the model. The electric resistivities were chosen at a frequency of 2 KHz. The major dimensions of the model and the material resistivity used are listed in Table 1.

TABLE 1

Parameters Used in the Models

| Parameters | Values |
| --- | --- |
| Heart model | |
| Right ventricle wall thickness | 5 mm |
| Left ventricle wall thickness | 15 mm |
| Septal thickness | 15 mm |
| Right ventricular volume | 40 ml |
| Left ventricular volume | 36 ml |
| Right ventricular curvature angle | 100 degrees |
| All models | |
| Blood resistivity at 2 KHz | 150 ohm.cm |
| Cardiac tissue resistivity at 2 KHz | 750 ohm.cm |
| Electrode resistivity 36 | 0.0001 ohm.cm |
| Ring electrode diameter | 2 mm |
| Ring electrode thickness | .2 mm |
| Electrode spacing | 10 mm |

The models were meshed such that there were higher mesh densities in regions where the electric potential gradients were high. In addition, meshing was done in such a way that the model geometry was well approximated in the meshed model. The solution was at first found with a low mesh density. The mesh density was progressively increased until no significant change in the result was observed.

The constant current loads were applied to the insides of the electrodes and the potential distribution within the model was solved using, for example, the Jacobi conjugate-gradient-out-of-core nonlinear solver with a wavefront capacity of 1,000 in an SGI-Onyx work station, although any other suitable method may be employed using any other suitable platform.

The primary finite-element solution was a set of nodal voltages. Elemental electric-field gradient and current density were derived from the primary solution. The catheter was positioned in a curved orientation within the right ventricular chamber and the electric potential along the catheter was determined. Knowing the electrode spacing which was assumed to be 1 cm for all simulations unless otherwise stated, it was possible to determine the potentials at the sensing electrodes and hence make volume determinations with the simulated catheter in the same manner as a real measurement scenario.

Figure 5:
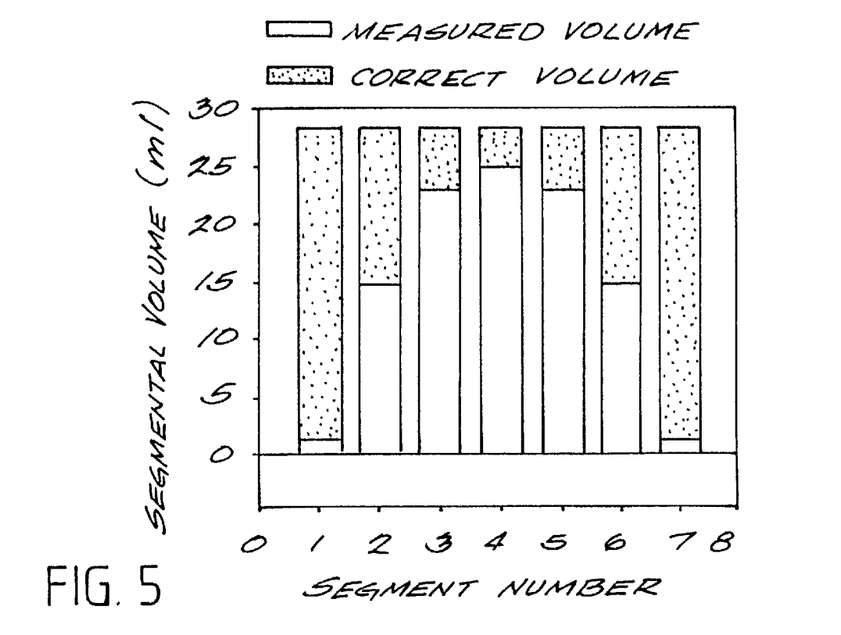
FIG. 5 shows the under estimation of ventricular volume resulting in errors introduced by a non-uniform electric field.
Figure 6:
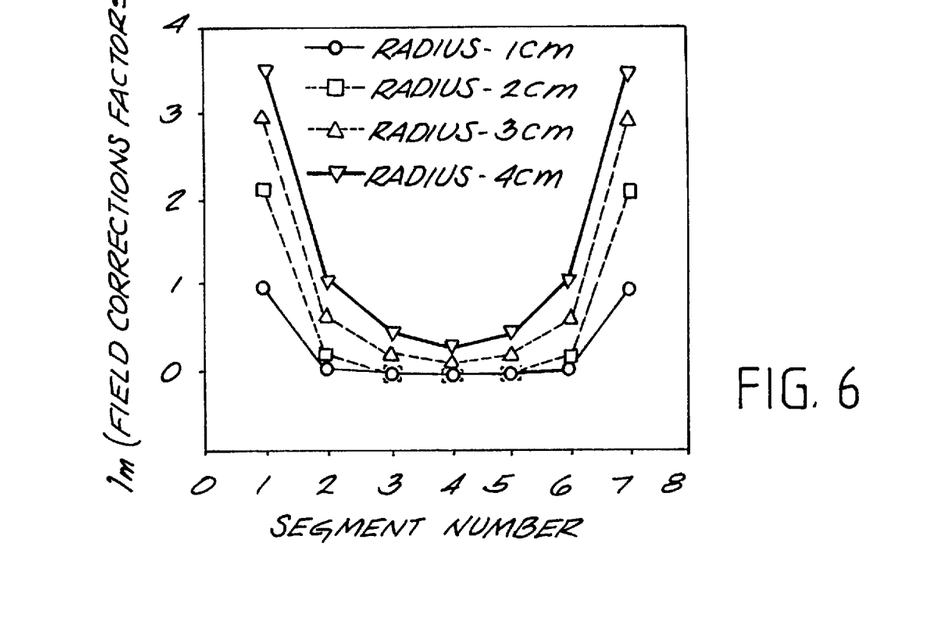
FIG. 6 shows correction factor CF to compensate for field non-uniformity errors.

From FIG. 2 it can be seen that the electric field gradient is high near the exciting electrodes and becomes more uniform as the distance from the exciting electrodes increases. A high electric gradient near the exciting electrodes results in an over estimation of segmental resistance in segments close to the exciting electrodes. Over estimation of resistance leads to an under estimation of volumes according to equation (2). The true segmental volume and the measured segmental volumes are shown in FIG. 5 where it can be seen that in segments near the exciting electrodes the volumes are under estimated. A field Correction Factor (CF), may be defined as the ratio of true segmental volume to measured segmental volume. The larger the field correction factor, the larger the field non-uniformity within the segment. It has been observed that field non-uniformity was affected by the segmental volume itself. FIG. 5 shows a set of field correction factors for different segments plotted against segmented volumes. It can be seen from FIG. 5 that for the same segment, the larger the segmental volume, the larger is the corresponding field correction factor.

Figure 7:
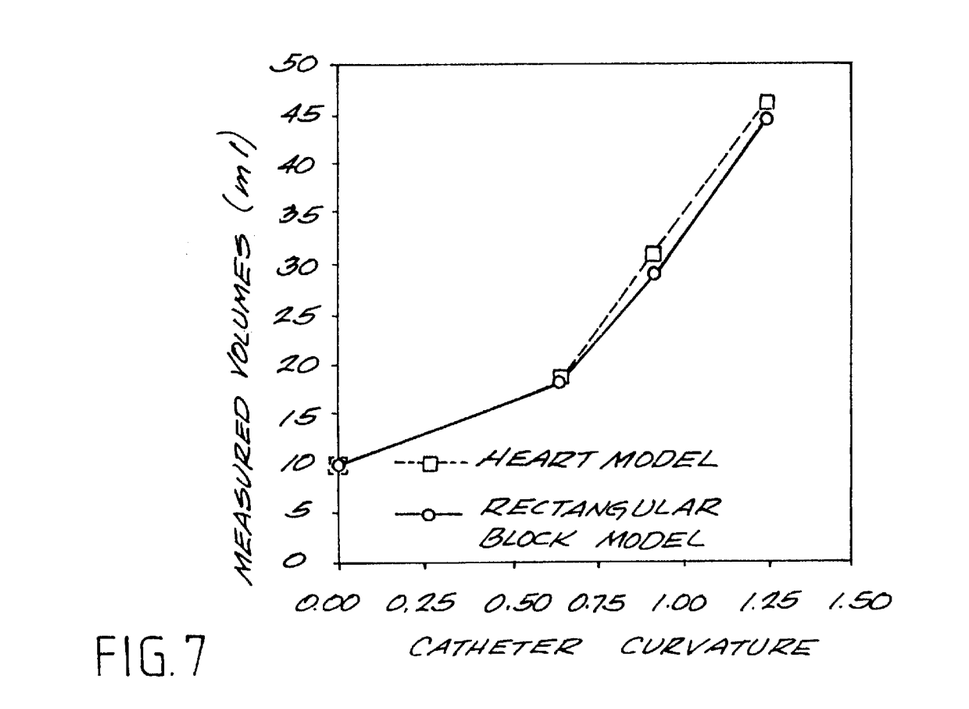
FIG. 7 shows the relationship between conductance catheter curvature and ventricular volume measurements.
Figure 8:
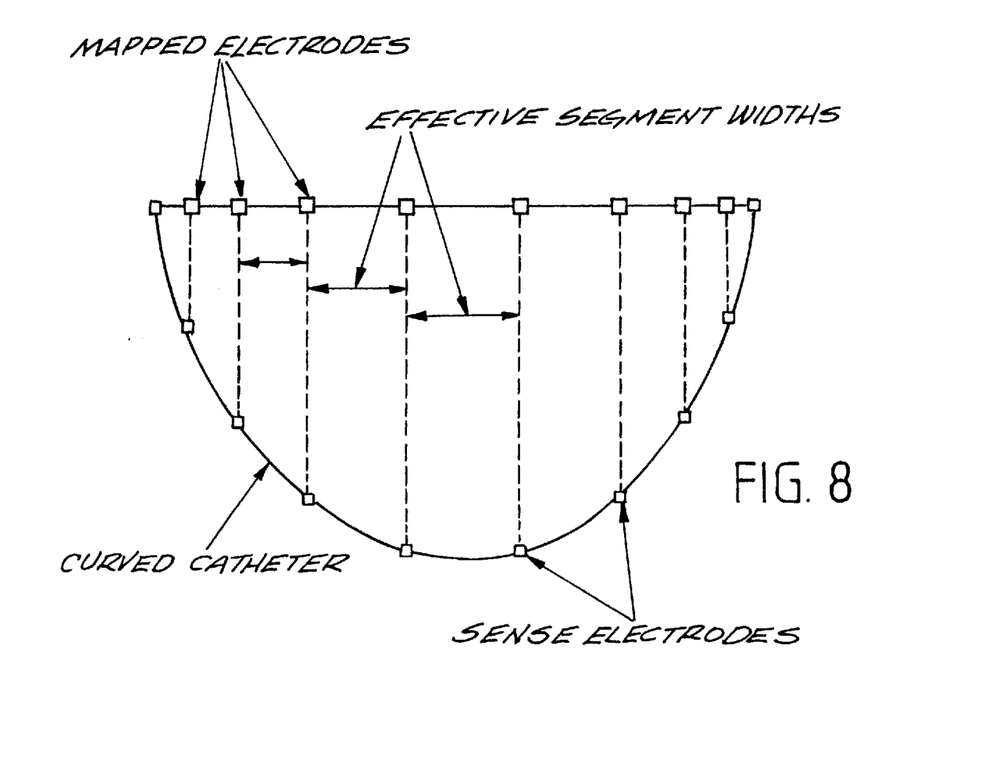
FIG. 8 shows the relationship between conductance catheter curvature and the width of ventricular volume segments.
Figure 9:
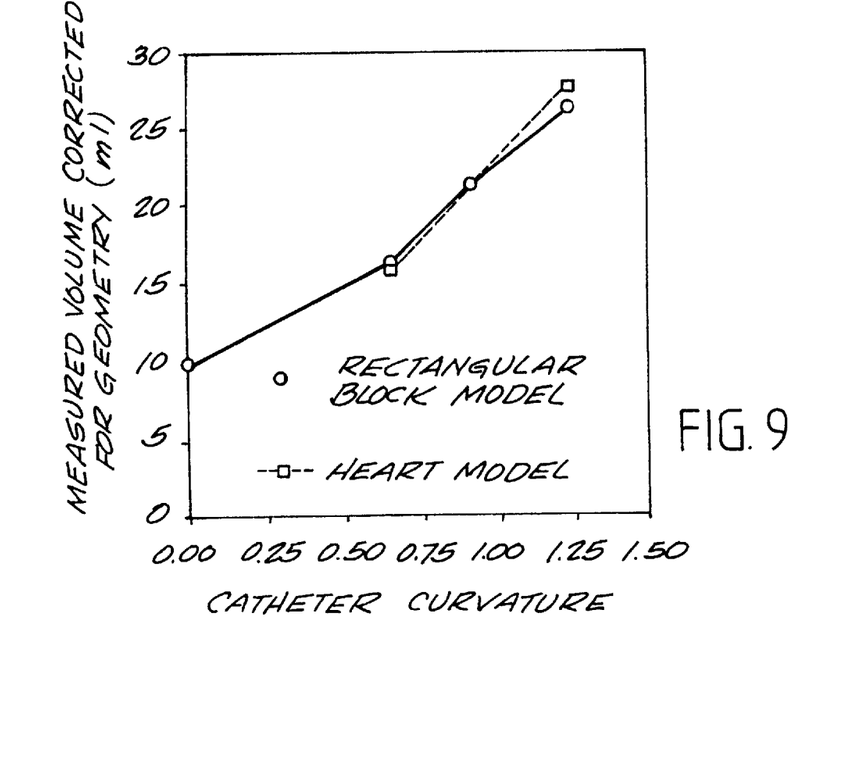
FIG. 9 shows the relationship between conductance catheter curvature and the measured volume after correction for effective width.

In all of the computer model analysis, the catheter shape was assumed to be semi-elliptical as shown in FIG. 4. X-ray pictures showing the catheter positioned in the right ventricle suggests an approximately elliptical shape when the catheter was properly positioned as shown in FIG. 2. The curvature of the catheter is defined as the ratio of the major axis radius to the minor axis radius. Physically, the minor axis radius represents half the distance between the centers of the AV valve 24 and the pulmonic valve 23. The major axis radius represents the distance from the base of the heart to the bent tip of the catheter 10 near the apex of the heart. Assuming an elliptical shape permits a single index of curvature to be defined. It has been found that for greater curvatures, the volume measured by the model also increased as shown in FIG. 7. One obvious effect of catheter curvature is that at larger curvature, the effective widths of the segments decrease so that the electrode spacing no longer represents the thickness of the segments as shown in FIG. 8. This can be corrected, as shown in FIG. 8, by geometrically mapping the positions of the electrodes on the curved catheter into a straight catheter. Geometrical mapping is helpful in determining the effective thickness of the volume segments. The effective thicknesses are assigned to variable "L" in equation (2) to determine the segmental volumes. But even after correction was made for the effective thickness of the segments, the measured volume still increased with curvature as shown in FIG. 9.

Figure 10:
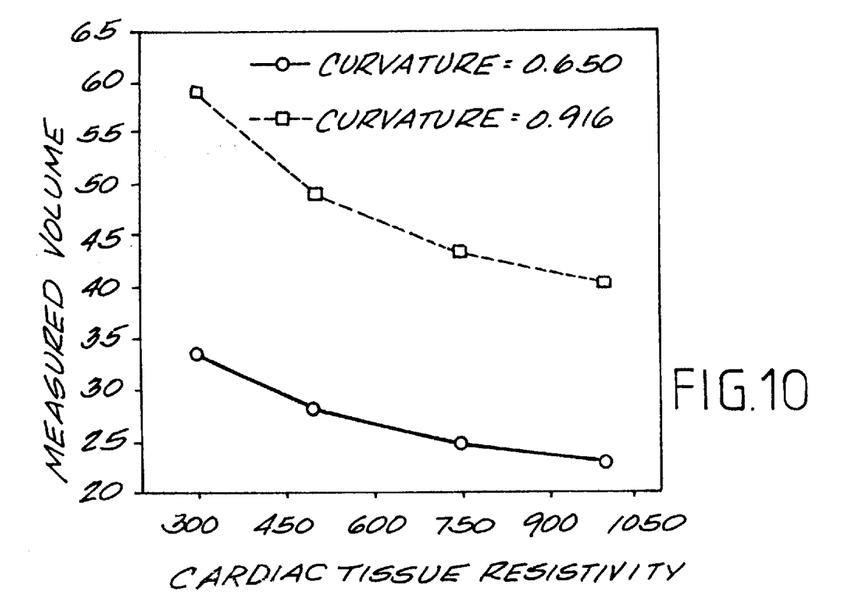
FIG. 10 shows the relationship between measured ventricular volume and cardiac tissue resistivity.

To see the effect of current leakage, the heart model was used with different tissue resistivities. Ventricular volume measured with the same catheter curvature but different tissue resistivities are plotted in FIG. 10. It can be seen that for lower tissue resistivities, larger volumes are measured. When tissue resistivity is lower a larger fraction of the injected current leaks out of the ventricular blood volume. This means that when leakage is higher, a lower current contributes to the blood resistance drop and the measured blood resistance is under estimated. This in turn leads to over estimation of segmental volumes. This effective leakage has been experimentally observed in previous studies.

If the field Correction Factor (CF) for all segments is determined, these can be multiplied by the measured volumes to determine the correct segmental volumes. Simulations with the heart model show that the field Correction Factors depend upon catheter curvature and segmental volume (FIGS. 7 and 8). It was also observed that the variations of field Correction Factors with catheter curvature and segmental volume are different for different segments. For each segment, sets of Correction Factors were found for different conditions of segmental volume and catheter curvatures. For each set of segmental volumes, the field correction factors were found for different catheter curvatures. Catheter curvature was also varied over a range that was expected in the right ventricular volume measurement. Once the field Correction Factors over a range of catheter curvatures and segmental volumes were found, two-dimensional interpolations can be used to find the field Correction Factor for any catheter curvature and segmental volume.

In the calculation of field Correction Factors, the effective widths of segments due to catheter curvature are incorporated. The effective widths of segments were found by geometrically projecting the positions of the sensing electrodes into a straight line that joins the exciting electrodes. By incorporating the different widths of the segments into the calculation of field correction factors, it is possible to correct for field non-uniformity and catheter curvature in the same step.

The field and curvature correction methods were verified in the heart model. For three different catheter curvatures, the field Correction Factors were found by interpolation and multiplied through the measured segmental volumes to arrive at the corrected volumes. The results are given in Table 2.

TABLE 2

Field and Curvature Corrections Applied to the Heart Model for Three Curvatures with five, Six and Seven Segments within the Ventricle

|  | Measured Volume (mL) | Correction Factor | Corrected Segmental Volume (mL) | True Segmental Volume (mL) |
| --- | --- | --- | --- | --- |
| 0/650 | | | | |
| Segment 1 | 1.62 | 3.20 | 5.18 | 4.77 |
| Segment 2 | 4.91 | 1.90 | 9.31 | 10.07 |
| Segment 3 | 5.42 | 1.85 | 10.03 | 10.78 |
| Segment 4 | 4.90 | 1.90 | 9.30 | 10.07 |
| Segment 5 | 1.70 | 3.20 | 5.44 | 4.77 |
| TOTAL VOLUME | 18.55 | — | 39.26 | 40.46 |
| 0.916 | | | | |
| Segment 1 | 1.62 | 1.9 | 3.078 | 2.605 |
| Segment 2 | 5.72 | 1.15 | 6.578 | 7.365 |
| Segment 3 | 8.10 | 1.13 | 9.150 | 10.26 |
| Segment 4 | 8.00 | 1.13 | 9.040 | 10.26 |
| Segment 5 | 5.76 | 1.15 | 6.624 | 7.365 |
| Segment 6 | 1.60 | 1.9 | 3.040 | 2.605 |
| TOTAL VOLUME | 30.08 | — | 37.51 | 40.46 |
| 1.249 | | | | |
| Segment 1 | 1.6 | 1.1 | 1.76 | 1.444 |
| Segment 2 | 6.5 | 0.75 | 4.875 | 4.916 |
| Segment 3 | 9.3 | 0.9 | 8.370 | 8.700 |
| Segment 4 | 11.3 | 0.9 | 10.35 | 10.35 |
| Segment 5 | 9.5 | 0.9 | 8.55 | 8.700 |
| Segment 6 | 6.5 | 0.75 | 4.875 | 4.916 |
| Segment 7 | 1.55 | 1.1 | 1.705 | 1.444 |
| TOTAL VOLUME | 46.2 | — | 40.31 | 40.46 |

Expression (2) above would provide the volume of each segment with the total volume comprising the sum of the segments. However, in actual practice, a portion of the injected current I leaks through surrounding tissues, especially cardiac tissue. Leakage of current through cardiac tissue leads to an over estimation of segmental volume. The present invention takes advantage of the differential electrical properties of cardiac tissue and blood to correct for errors introduced as a result of leakage current.

In the frequency range of 1–100 KHz, resistivity and the dielectric constant of blood remain constant while that of cardiac tissue changes. On the other hand, the resistivity of cardiac tissue and its dielectric constant decrease as frequency increases within this range. For example, an increase in frequency from 1 KHz to 50 KHz, the conductivity of blood remains constant while that of cardiac tissue increases by 40%. This permits the use of multiple frequencies to establish electric fields and make volume measurements so that the fraction of the total injected current that leaks through the Cardiac tissue can be estimated.

Figure 11:
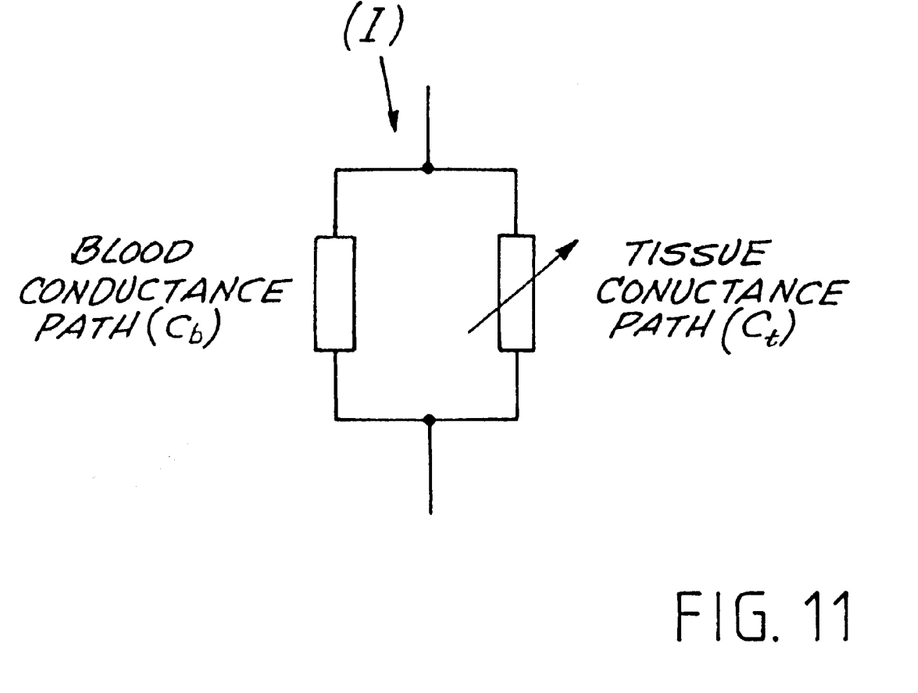
FIG. 11 shows the total conductance for the current flowing between the exciting electrodes of a conductance catheter.
Figure 12:
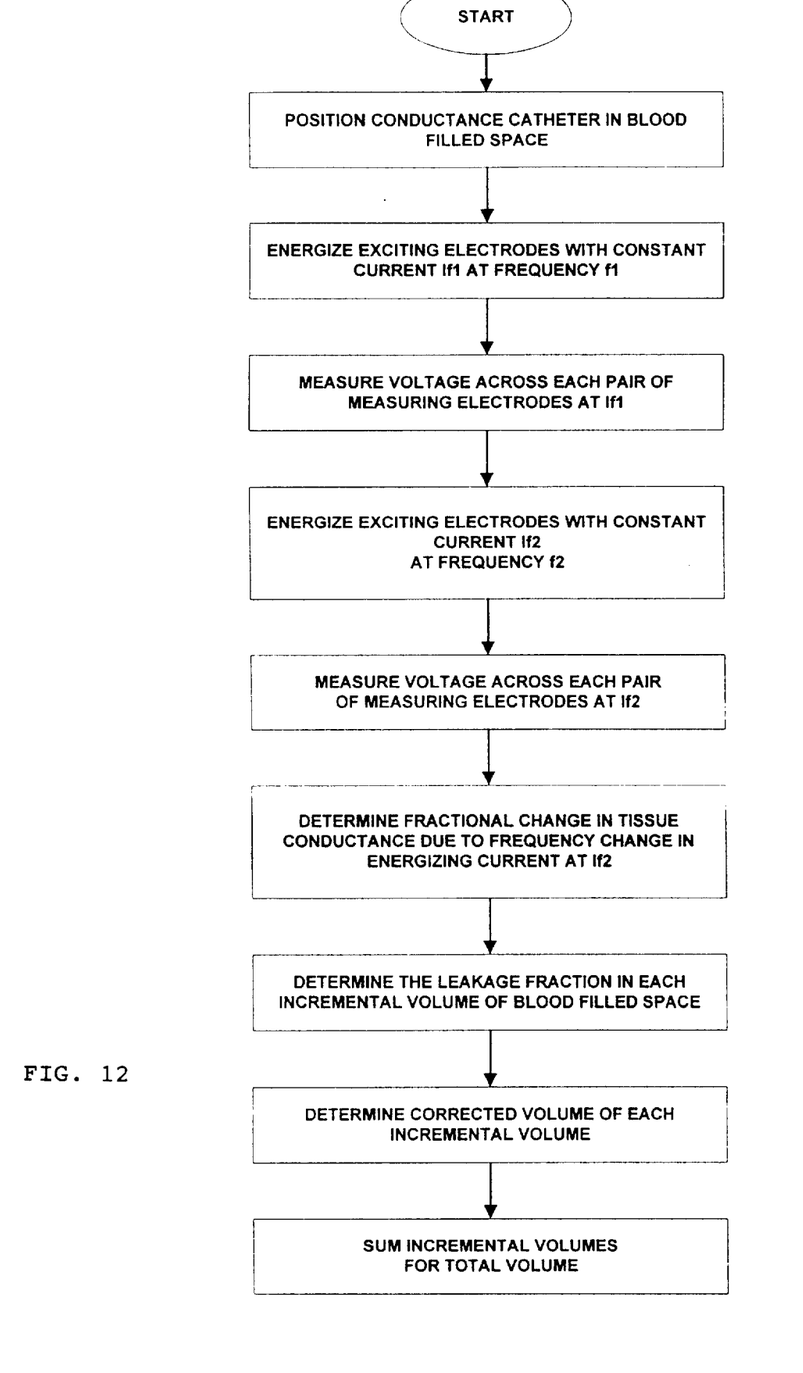
FIG. 12 is a flow diagram illustrating the method according to the invention.

The total measured conductance of each of the segments a–f of the blood filled space consist of the parallel combination of a tissue conductive part and a blood conductive part as shown in FIG. 11. The total conductance is found by summing the measured segmental conductances. The fraction of the total conductance that comprises the cardiac tissue part is termed the bulk leakage fraction (BLF) which is determined as follows:

$$BLF = C_t/C_{tot} \tag{5}$$

where $C_{tot} = C_b + C_t$, $C_t$=total tissue conductance path,
$C_b$=total blood conductance path,
$C_{tot}$=total measured conductance.

BLF also gives the fraction of the total injected current that leaks into the cardiac tissue. If a measurement of total conductance is made for the same ventricular volume, but at two different frequencies within the range 1–100 KHz, then the change in total conductance is essentially due the change in tissue conductance at different frequencies. If f1 is the frequency of the current supplied by the AC current stimulator 25 that is used to make normal volume measurements and f2 is a different frequency of the applied current within the range 1–100 KHz, then $$C_{tot}(f1) = C_b + C_t \tag{6}$$

and $$C_{tot}(f2) = C_b + C_t + \alpha C_t \tag{7}$$

where
$C_{tot}(f1)$=total measured conductance at f1 (normal measuring frequency),
$C_{tot}(f2)$=total measured conductance at f2, and
$\alpha$=fractional change in tissue conductance due to change in frequency.

If $p = C_t/(C_b + C_t)$ then $$\alpha p = [C_{tot}(f2) - C_{tot}(f1)]/C_{tot}(f1) = \alpha C_t/(C_b + C_t) \tag{8}$$

The fractional change in tissue conductance, a, is obtained from the cardiac tissue conductivity-frequency curve which is established from the literature. The fractional change in tissue conductivity when the frequency of stimulation is changed from f1 to f2 is determined from the frequency characteristic curve. Because the measurements are made at f1 and f2 for the same ventricular volume, the fractional change in tissue conductivity is the same as a. The ratio p should ideally be the same as the bulk leakage fraction (BLF). However, because the electric field established by the exciting electrodes is not uniform, p is different from BLF. Specifically, the difference is due to the fact that the non-uniformity of the field does not affect both the tissue part and the blood part in FIG. 2 equally. Computer models using finite element simulation shows that P is proportional to BLF by a factor of 1.375 or $$BLF = 1.375p \tag{9}$$

Once the BLF is found, the individual leakage fractions in the segments that are used for volume measurement can be found. Individual volume segments have different leakage fractions because the effect of electric field non-uniformity is different in different segments. The relationship of BLF to the individual segmental leakage fractions was established with computer models using finite element simulations. This relationship is as follows:

$$LF_i = a_i BLF + b_i \tag{10}$$

where
$LF_i$=leakage fractions in segment 'i'
$a_i$ and $b_i$ are constant factors for segment 'i' as determined by computer simulation, and are given in the Table 3 below.

TABLE 3

| Constants | Segment 1 | Segment 2 | Segment 3 |
|---|---|---|---|
| a | 0.4386 | 0.996 | 1.010 |
| b | −0.1484 | −0.0014 | 0.0541 |

If N is the total of measuring segments, then the constants $(a_i, b_i)$ for the segment N−i+1 is the same as those for segment 'i'. The leakage fractions in each fraction can be determined in each sample point of volume measurement. Once the leakage fractions in each segment is computed, leakage corrected segmental volumes are computed as follows:

$$LCVol_i = Vol_i(1 - LF_i) \tag{11}$$

where
$LCVol_i$=leakage corrected volume of segment 'i',
$Vol_i$=volume computed by equation $Vol_i = \rho L^2/R_i$
The resistivity $\rho$ of the blood in the volume measurement is determined by the expression:

$$\rho = V/IKc \tag{12}$$

where
I=the current between the exciting electrodes,
V=the potential measured between the exciting electrodes, and
Kc=a calibration ratio A typical conductance catheter has electrodes spaced about 10 mm from edge to edge. The electrodes may be about 2.5 mm in both length and diameter and may be formed of any suitable material, such as, stainless steel or an alloy of 90% platinum and 10% iridium. The catheter body is an extruded plastic material having a plurality of lumens. A plastic stiffening member is preferably disposed in one of the lumens and the conductors to the electrodes 15–22 are disposed in a different lumen.

The ratio of the applied current to the measured voltage bears a constant ratio to the true resistivity of the blood. This constant calibration ratio must be determined by the processor 32 for each specific electrode dimension and spacing and can be established by using a standard liquid of known resistivity or by computer simulation. The calibration ratio remains substantially constant as long as the electrodes are close to each other and there is a sufficient volume of blood surrounding the electrodes. Once the calibration ratio Kc is established, the true resistivity R(rho) Of the blood can be determined.

If a two point current source is positioned at a unit distance apart in an infinite volume of material with uniform resistivity and a constant current injected by the source is I and the potential drop across the source is V, it can be mathematically shown that the ratio V/I is the true conductivity of the material divided by 3.14. As a result, by dividing the ratio V/I by 3.14 (the calibration ratio), the true resistivity of the material can be determined.

For different electrode geometry, the calibration ratio will differ from 3.14. Computer simulations and experimental evidence has shown that there is no appreciable change in the calibration ratio as long as the electrode dimensions and the material volume around the electrodes has of the order of three times or more than the electrode spacing. It is also been found that the calibration ratio is predominantly dependent on the size of the electrodes rather than electrode spacing.

The true resistivity of the patient's blood may also be determined by drawing a quantity of blood and making the measurement directly.

For a particular catheter curvature and a set of raw segmental volumes, correction factors can be determined by an interpolation method and a field function method. Using the interpolation method, the pre-computed correction factors from finite element model simulation is used to describe two dimensional variations of correction factors for each segment. For each segment, variations in the Correction Factor can be described with raw volumes and catheter curvatures. Two dimensional interpolation (linear or higher order) may be used to find the correction factor for a segment for a particular catheter curvature and segmental raw volume. The segmental volume is then multiplied by the found correction factor to obtain the field corrected volumes. This procedure is repeated for all measured segments.

In the field function method, the pre-computed correction factors are used to construct functions that describe the variations of correction factors with respect to catheter curvature and segmental raw volumes. The functions are constructed by using a least squares curve-fitting algorithm. For a particular catheter curvature, the correction factors are linearly related to the measured raw volumes. The linear relation was different for different segments. The correction factor for the $i^{th}$ segment can be derived from the expression:

$$CF_i = a_i RV_i + b_i \qquad (14)$$

where $CF_i$=Correction factors for segment 'i'
$RV_i$=Raw volume of segment 'i'
$a_i$=slope for the $i^{th}$ segment
$b_i$=intercept for the $i^{th}$ segment The slope ($a_i$) and the intercept ($b_i$) of equation (14) are determined from the catheter curvature.

$$a_i = m_i/Cur + n_i \qquad (15)$$

$$b_i = p_i Cur + q_i \qquad (16)$$

where

'Cur' is the catheter curvature and constants $m_i$, $n_i$, $p_i$ and $q_i$ depend on the segment number 'i'. If N is the total number of measuring segments, then the constants (m,n,p,q) for segment 'N−i+1' is the same as those for segment 'i'. This is because of the symmetric nature of the elliptical shape of the catheter. The constants for i=1,2 and 3 are given in the Table 4 below.

TABLE 4

Constants Used in the Field Functions

| Segment #(i) | m | n | p | q |
|---|---|---|---|---|
| 1 | 6.431 | −2.404 | 6.195 | −10.261 |
| 2 | 0.1062 | −0.0512 | −1.867 | 2.812 |
| 3 | 0.02877 | 0.01354 | −1.606 | 2.507 |

Thus, once the catheter position is fixed, knowing the curvature, the slope and intercept of equation (14) can be determined for each measuring segment. With equation (14) established, it is possible to find the correction factor for any raw segmental volume. To further improve accuracy of the correlation factors, an empirical modifying factor must be multiplied to the Correction Factor. The modifying factor ($mf_i$) for segment 'i' is given by the expression:

$$mf_i = (1 + sm.i.(i)) \qquad (17)$$

and $$sm = (vd - 4.0).Cur^3/(2.vd) \qquad (18)$$

where vd=valve distance and Cur=the catheter curvature.

Compared to the interpolation method, the field function method is faster in computing real-time correction factors. In determining the real-time correction for field non-uniformity, the following steps are performed as shown in FIG. 11:

1. Choosing the exciting electrodes to be near the tricuspid and aortic valves;
2. Determine the number of segments within the ventricle;
3. Energize the exciting electrodes;
4. Measure the voltage across measuring electrodes;
5. Determining valve distance or the shortest distance between the exciting electrodes;
6. Determine catheter curvature;
7. Determine raw segmental volumes;
8. Determine the correction factors for each segment for a particular catheter curvature by either the interpolation method or the field function method; and
9. Multiply the raw volumes by the correction factors to obtain the corrected segmental volumes.

While only a single embodiment of the invention has been illustrated and described, it is not intended to be limited thereby, but only by the scope of the appended claims.

We claim:

1. A method of determining cardiac volume by means of a catheter adapted to be positioned in a blood filled chamber of a human heart the catheter comprising an elongated body having a distal end and proximal end, a plurality of spaced electrodes arrayed on the outer surface of the catheter and being spaced apart a predetermined distance from each other to define a proximal electrode and a distal electrode and a plurality of electrodes disposed therebetween, pairs of adjacent electrodes between the distal and proximal electrodes defining volume segments within the chamber, the method comprising the steps of positioning the catheter in a blood filled chamber of a human heart, the catheter assuming an arcuate configuration so that the segments of the catheter between adjacent electrodes are curved, providing a constant alternating electrical excitation to the distal and proximal electrodes, measuring an electrical parameter between pairs of adjacent electrodes located between the distal and proximal electrodes while the distal and proximal electrodes are energized with the electrical excitation, determining the uncorrected volume of each volume segment from the measured electrical parameters, determining a correction factor CF for each volume segment from the accurate curvature of the segment, and applying the correction factor CF to the uncorrected volume of each volume segment to provide a corrected volume for each segment.

2. The method set forth in claim 1 and including the step of determining the slope $a_i$ and intercept $b_i$ of the catheter segments, wherein the correction factor CF is determined from the uncorrected volume and the slope and intercept of the catheter segment in the volume segment.

3. The method set forth in claim 2 and wherein the correction factor is derived from the expression:

$$CF_i = a_i RV_i + b_i$$

where

CFi=Correction factors for segment 'i'
$a_i$=slope for the $i^{th}$ segment
$b_i$=intercept for the $i^{th}$ segment
$RV_i$=Uncorrected or raw volume of segment i.

4. The method set forth in claim 3 wherein the step of determining the slope $a_i$ and the intercept $b_i$ from the curvature of the catheter is determined as follows:

$$a_i = m_i/Cur + n_i$$

$$b_i = p_i/Cur + q_i$$

where

'Cur' is the catheter curvature and constants $m_i$, $n_i$, $p_i$ and $q_i$ depend on the segment number 'i'.

5. The method set forth in claim 1 including the step of determining catheter curvature wherein the correction factor CF for each segmental volume is determined from the curvature of the catheter segment in the volume segment.

6. The method set forth in claim 5 wherein the electrical excitation is an alternating current and the electrical parameter is the potential between pairs of adjacent electrodes.

7. An apparatus for determining cardiac volume comprising a catheter adapted to be positioned in a blood filled chamber of a human heart, the catheter comprising an elongate body having a distal end and a proximal end, a plurality of spaced electrodes arrayed on the outer surface of the catheter and being spaced apart a predetermined distance from each other to define a proximal electrode and a distal electrode and a plurality of electrodes disposed therebetween, pairs of adjacent electrodes between the distal and proximal electrodes defining volume segments within the chamber, said catheter adapted to assume a curved configuration within a chamber so that segments of the catheter between adjacent electrodes are curved, means for providing a constant alternating electrical excitation to the distal and proximal electrodes, means for measuring an electrical parameter between pairs of adjacent electrodes located between the distal and proximal electrodes while the distal and proximal electrodes are energized with the electrical excitation, a processor coupled to the means for measuring the electrical parameter for determining the uncorrected volume of each volume segment from the measured electrical parameter, and for determining a correction factor for each volume segment from the curvature of the catheter segment therein and for applying the correction factor for each volume segment to the uncorrected volume of that segment to provide a corrected segmental volume for each volume segment.

8. The apparatus set forth in claim 7 wherein the processor is operative to determine the slope $a_i$ and $b_i$ intercept of the curved catheter segments, and to determine the Correction Factor from the uncorrected volume and the slope and intercept of the curved catheter segments.

9. The apparatus set forth in claim 8 wherein said processor is operative for deriving the Correction Factor from the expression:

$$CF_i = a_i RV_i + b_i$$

where

CFi=Correction factors for segment 'i'
$a_i$=slope for the $i^{th}$ segment
$b_i$=intercept for the $i^{th}$ segment
R=the resistance of the volume segment
$V_i$=the measured voltage across the $i^{th}$ segment.

10. The apparatus set forth in claim 9 wherein the processor is operative to determine the slope $a_i$ and the intercept $b_i$ from the curvature of the catheter as follows:

$$a_i m_i/Cur + n_i$$

$$b_i = p_i/Cur + q_i$$

where

'Cur' is the catheter curvature and constants $m_i$, $n_i$, $p_i$ and $q_i$ depend on the segment number 'i'.

11. The apparatus set forth in claim 7 and including means for determining catheter curvature, the processor being operative to determine the correction factor for each volume segment from the curvature of the catheter segment therein.

12. The apparatus set forth in claim 11 wherein the means for providing a constant alternating electrical excitation is an alternating current source and the means for measuring an electrical parameter comprises means for measuring the potential between pairs of adjacent electrodes.

13. A method of determining cardiac volume comprising the steps of positioning a conductance catheter in a blood filled chamber of a human heart, the catheter having a plurality of spaced apart electrodes, positioning the catheter in a curved configuration so that a first one of spaced apart electrodes is adjacent to the tricuspid valve and a second one of the spaced electrodes is positioned adjacent to the aortic valve, determining the number of electrodes between the first and second electrodes, energizing the first and second electrodes, determining a voltage between adjacent pairs of electrodes between the first and second electrodes, the adjacent pairs of electrodes defining segmental volumes within the chamber, determining a distance between the exciting electrodes, determining catheter curvature, determining uncorrected segmental volumes of the chamber as defined by the adjacent pairs of electrodes, determining correction factors for each segmental volume for the catheter curvature between adjacent pairs of electrodes defining the segmental volumes, and multiplying the uncorrected segmental volume of each volume segment by the correction factor for that segment to determine the true segmental volume.

14. The method set forth in claim 13 including the steps of determining the slope $a_i$ and intercept $b_i$ the of catheter segments, wherein the correction factor CF is determined from the uncorrected volume and the slope and intercept of the catheter segment in the volume segment.

15. The method set forth in claim 14 and wherein the step of determining the correction factor is determined from the expression:

$$CF_i = a_i RV_i + b_i$$

where
- $CF_i$ = Correction factors for segment 'i'
- $a_i$ = slope for the $i^{th}$ segment
- $b_i$ = intercept for the $i^{th}$ segment
- R = the resistance of the volume segment
- $V_i$ = the measured voltage across the $i^{th}$ segment.

16. The method set forth in claim 15 and wherein the step of determining the slope $a_i$ and the intercept $b_i$ from the curvature of the catheter is determined as follows:

$$a_i = m_i/Cur + n_i$$

$$b_i = p_i/Cur + q_i$$

where
'Cur' is the catheter curvature and constants $m_i$, $n_i$, $p_i$ and $q_i$ depend on the segment number 'i'.

* * * * *